| (12) | United States Patent | (10) Patent No.: US 11,395,735 B2 |
|---|---|---|
| | Zhao et al. | (45) Date of Patent: Jul. 26, 2022 |

(54) VALVE STENT AND VALVE PROSTHESIS

(71) Applicant: SHANGHAI MICROPORT CARDIOFLOW MEDTECH CO., LTD., Shanghai (CN)

(72) Inventors: Chunxia Zhao, Shanghai (CN); Ming Yang, Shanghai (CN); Guoming Chen, Shanghai (CN); Yu Li, Shanghai (CN)

(73) Assignee: SHANGHAI MICROPORT CARDIOFLOW MEDTECH CO., LTD., Shanghai (CN)

( * ) Notice: Subject to any disclaimer, the term of this patent is extended or adjusted under 35 U.S.C. 154(b) by 0 days.

(21) Appl. No.: 16/647,153

(22) PCT Filed: Aug. 17, 2018

(86) PCT No.: PCT/CN2018/100917
§ 371 (c)(1),
(2) Date: Mar. 13, 2020

(87) PCT Pub. No.: WO2019/052305
PCT Pub. Date: Mar. 21, 2019

(65) Prior Publication Data
US 2021/0022854 A1 Jan. 28, 2021

(30) Foreign Application Priority Data

Sep. 14, 2017 (CN) .......................... 201710829301.9

(51) Int. Cl.
*A61F 2/24* (2006.01)
(52) U.S. Cl.
CPC .......... *A61F 2/2418* (2013.01); *A61F 2/2409* (2013.01); *A61F 2220/0016* (2013.01)

(58) Field of Classification Search
CPC ..... A61F 2/2409; A61F 2/2412; A61F 2/2418
See application file for complete search history.

(56) References Cited

U.S. PATENT DOCUMENTS

| 2012/0053685 A1 | 3/2012 | Cerf et al. |
| 2013/0211508 A1* | 8/2013 | Lane .................. A61F 2/2427 623/2.11 |

(Continued)

FOREIGN PATENT DOCUMENTS

| CN | 101352376 A | 1/2009 |
| CN | 101961273 A | 2/2011 |

(Continued)

*Primary Examiner* — Suba Ganesan
(74) *Attorney, Agent, or Firm* — Muncy, Geissler, Olds & Lowe, PC

(57) ABSTRACT

A valve stent and a valve prosthesis. The valve stent is in the shape of a mesh tube, and has a compressed state and an expanded state. The valve stent includes an inflow tract structure, a transition tract structure, an outflow tract structure, and a barb structure. The transition tract structure has a fifth end portion, a sixth end portion, and a first middle section. In the expanded state, the diameters of the radial sections of the fifth end portion and the sixth end portion are greater than the diameter of the radial section of the first middle section of the transition tract structure. The outflow tract structure has a seventh end portion and an eighth end portion. The seventh end portion of the outflow tract structure is fixedly connected to the sixth end portion of the transition tract structure, and the eighth end portion is a free end. The barb structure is disposed on the transition tract structure and the outflow tract structure, and protrudes towards the outside of the transition tract structure and/or the outflow tract structure. The valve stent and the valve prosthesis can be stably anchored on natural valves.

17 Claims, 16 Drawing Sheets

(56) References Cited

U.S. PATENT DOCUMENTS

2013/0304200 A1* 11/2013 McLean ................ A61F 2/2436
                                                                                                                        623/2.18
2014/0214157 A1* 7/2014 Bortlein ................ A61F 2/2427
                                                                                                                        623/2.11
2015/0196390 A1* 7/2015 Ma ........................ A61F 2/2418
                                                                                                                        623/2.17
2017/0325948 A1* 11/2017 Wallace ................ A61F 2/2409

FOREIGN PATENT DOCUMENTS

| CN | 104720937 A | 6/2015 |
|----|-------------|--------|
| CN | 106794063 A | 5/2017 |
| CN | 107334563 A | 11/2017 |
| JP | 2017-506549 A | 3/2017 |
| WO | WO-2015/128747 A2 | 9/2015 |
| WO | WO-2015/132667 A1 | 9/2015 |
| WO | WO-2015/177655 A1 | 11/2015 |
| WO | WO-2016/172349 A1 | 10/2016 |
| WO | WO-2018/136959 A1 | 7/2018 |

* cited by examiner

VALVE STENT AND VALVE PROSTHESIS

TECHNICAL FIELD

The present application relates to the technical field of medical instruments and, more specifically, to a valve stent and a valve prosthesis.

BACKGROUND

The heart contains four cardiac chambers, wherein the left atrium and left ventricle are on the left side of the heart, and the right atrium and right ventricle are on the right side of the heart. A ventricular inflow tract structure is formed between the atrium and the ventricle, a left ventricular outflow tract structure is formed by the left ventricle and the aorta, and a right ventricular outflow tract structure is formed by the right ventricle and the pulmonary artery. There are valves at the ventricular inflow tract structure, the left ventricular outflow tract structure, and the right ventricular outflow tract structure. The valve has a "one-way valve" function to ensure the normal flow of blood in the cardiac chambers. When a problem occurs in the valve, the heart hemodynamics change, and the heart functions abnormally, which is called valvular heart disease.

With the development of social economy and the aging of the population, the incidence of valvular heart disease is increased significantly. Researches show that the incidence of valvular heart disease in the elderly population over the age of 75 is up to 13.3%. Conventional surgical treatment is still the first choice for patients with severe valvular disease. However, for elderly patients with multi-organ diseases, a history of thoracotomy, and poor cardiac function, conventional surgery has a high risk and a high mortality rate, and some patients don't even have a chance for surgery. Due to advanced age, complications, and left ventricular dysfunction, up to 50% of symptomatic patients with severe mitral regurgitation are not eligible for conventional mitral valve repair or replacement. As a result, interventional operations that can effectively reduce the surgical risk and mortality have gradually gained recognition. However, conventional interventional operations rely on Cardiopulmonary Bypass (CPB), and the operation lasts longer. In contrast, transcatheter valve implantation and transcatheter valve repair have the advantages of no need for thoracotomy, minimal trauma, and rapid patient recovery, and are therefore widely used in interventional operations.

In recent years, transcatheter aortic valve implantation has been developed to perform interventional replacement of aortic valves, and better therapeutic effects are achieved. In Western countries, applicable population of the transcatheter aortic valve implantation gradually transitions from the high-risk population to the middle- and low-risk population. In China, the transcatheter aortic valve implantation is gradually promoted with many independent innovative research brands.

Compared with the transcatheter aortic valve implantation, the transcatheter mitral valve implantation and the transcatheter tricuspid valve implantation face more challenges. The mitral valve, also called a bicuspid valve, is located at the left ventricular inflow tract structure. The main structure is the mitral valve complex, including the mitral annulus, leaflets, chordae tendineae, left papillary muscle, right papillary muscle, and myocardium. The leaflets of the mitral valve are two anterior and posterior valves attached to the periphery of the left ventricular ostium. The leaflets of the mitral valve are connected to the anterior and posterior papillary muscles by means of chordae tendineae. The papillary muscles are attached to the ventricular wall. The tricuspid valve, as the atrioventricular valve of the right heart, has a structure similar to that of the mitral valve, and also includes leaflets, annulus, chordae tendineae, papillary muscles, and myocardium.

Due to the complexity in structures of the mitral and tricuspid valve, after a mitral valve prosthesis and a tricuspid valve prosthesis are implanted into the heart, whether anchorage is stable has become an urgent problem to be solved for the transcatheter mitral valve implantation and the transcatheter tricuspid valve implantation.

SUMMARY OF THE INVENTION

An objective of the present application is to provide a valve stent and a valve prosthesis, for solving the technical problem of unstable anchorage of the existing valve stent and the valve prosthesis.

To solve the foregoing technical problem, the present application provides a valve stent, wherein the valve stent is a self-expanding stent, is shaped as a mesh tube, and has a compressed state and an expanded state;

the valve stent comprises an inflow tract structure, a transition tract structure, an outflow tract structure, and a barb structure; the inflow tract structure, the transition tract structure, and the outflow tract structure are connected sequentially, and the barb structure is disposed on the transition tract structure and/or the outflow tract structure;

the inflow tract structure comprises a ring structure having a first end portion and a second end portion, and the second end portion is a free end; in the expanded state, a diameter of a radial section of the first end portion of the ring structure is smaller than a diameter of a radial section of the second end portion of the ring structure;

the transition tract structure has a fifth end portion, a sixth end portion, and a first middle section; the fifth end portion and the sixth end portion are located at two ends of the first middle portion in an axial direction of the first middle portion; the fifth end portion is fixedly connected to the first end portion of the ring structure; the sixth end portion is away from the inflow tract structure; in the expanded state, diameters of radial sections of the fifth end portion and the sixth end portion are greater than a diameter of a radial section of the first middle section of the transition tract structure;

the outflow tract structure has a seventh end portion, an eighth end portion, and a second middle section; the seventh end portion and the eighth end portion are located at two ends of the second middle portion in an axial direction of the second middle portion; the seventh end portion of the outflow tract structure is fixedly connected to the sixth end portion of the transition tract structure; the eighth end portion is away from the transition tract structure and the inflow tract structure, and the eighth end portion is a free end;

the barb structure protrudes towards an outside of the transition tract structure and/or an outside of the outflow tract structure.

Optionally, the barb structure comprises a plurality of second barbs and a plurality of first barbs; each of the second barbs and the first barbs has a fixation end; one end of each of the second barbs and the first barbs away from the fixation end is a free end; the fixation end of each of the second barbs is disposed on the transition tract structure, and each of the second barbs protrude from the fixation end thereof towards the outside of the transition tract structure; the fixation end of each of the first barbs is located on the outflow tract structure, and each of the first barbs protrude from the fixation end thereof towards the outside of the outflow tract structure.

Optionally, the fixation end of each of the second barbs is located on the sixth end portion of the transition tract structure, and the fixation end of each of the first barbs is located on the outflow tract structure.

Optionally, in the expanded state, a diameter of a radial section of the seventh end portion and a diameter of a radial section of the eighth end portion are smaller than a diameter of a radial section of the second middle section, a section with a maximum diameter among radial sections of the outflow tract structure is a first section, and each of the first barbs is located in the first section of the outflow tract structure.

Optionally, the valve stent comprises an extension structure having a ninth end portion and a tenth end portion, wherein the ninth end portion is fixedly connected to the ring structure, and the tenth end portion is away from the ring structure and the transition tract structure.

Optionally, an axial length of the extension structure is greater than an axial length of the ring structure after the valve stent is compressed.

Optionally, an axial length of the extension structure is smaller than an axial length of the ring structure after the valve stent is compressed.

Optionally, the inflow tract structure and the extension structure are staggered apart from each other in an axial direction after the valve stent is compressed.

Optionally, a maximum diameter of radial sections of the extension structure is smaller than a maximum diameter of radial sections of the ring structure.

Optionally, the ninth end portion of the extension structure is fixedly connected to the first end portion of the ring structure.

Optionally, the valve stent further comprises a plurality of lugs, wherein the tenth end portion of the extension structure is fixedly connected to the lugs.

Optionally, the extension structure comprises at least a group of fourth wave rod units, and the group of fourth wave rod units comprises a plurality of Y-shaped fourth wave rods.

Optionally, the valve stent comprises an extension structure having a ninth end portion and a tenth end portion, wherein the ninth end portion is fixedly connected to the transition tract structure, and the tenth end portion is away from the transition tract structure.

Optionally, in the expanded state, a sum of axial lengths of the outflow tract structure and the transition tract structure is in a range of 10 mm to 35 mm.

Optionally, a radial section of the ring structure of the valve stent has a shape of a circular ring, an elliptical ring, or a D-shaped ring.

The present application further provides a valve prosthesis, comprising the valve stent according to any one of claims 1 to 15, a prosthetic leaflet, and a suture skirt, wherein the prosthetic leaflet and the suture skirt are attached to the valve stent; the prosthetic leaflet is located inside the transition tract structure and the outflow tract structure; the suture skirt covers the ring structure, the transition tract structure, and the outflow tract structure; wherein a single blood channel, configured to allow blood to flow through an interior of the valve stent in a direction from the inflow tract structure to the outflow tract structure, is formed by the suture skirt and the prosthetic leaflet.

Optionally, the suture skirt is not attached to the extension structure.

The valve stent and the valve prosthesis provided by the present application have the following advantageous effects.

In the expanded state, the diameters of the radial sections of the fifth and sixth end portions of the transition tract structure are greater than the diameter of the radial section of the first middle section of the transition tract structure, that is, the transition tract structure is inwardly recessed. On the one hand, the recess is filled with the annulus and leaflets of the natural mitral valve after the valve stent is implanted in the natural mitral valve, which facilitates anchoring the valve stent on the natural mitral valve. On the other hand, the inwardly recessed shape of the transition tract structure facilitates matching with the shape of the annulus of the natural mitral valve, thereby facilitating the positioning of the valve stent and the deploy of the valve stent into the natural mitral valve by the surgeon. In addition, the recess is filled with the annulus and leaflets of the natural mitral valve, so that the valve stent is better covered by the annulus and leaflets of the natural mitral valve, thereby avoiding the blood flowing from the left atrium into the left ventricle through a gap between the natural mitral valve and the valve stent.

Moreover, the diameter of the second end portion of the ring structure is greater than the diameter of the first end portion. The ring structure extends the radial depth of the recess of the transition tract structure and increases the length of the recess along the central axis, so that more natural mitral valves are filled into the recess, further facilitating anchoring the valve stent on the natural mitral valve, and facilitating the deploy of the valve stent into the natural mitral valve by the surgeon.

In addition, the valve stent is anchored to the natural mitral valve by means of the barb structure and the inwardly recess formed by the transition tract structure and the ring structure, which can improve the anchoring effect of the valve stent, and meanwhile, the influence on the natural mitral valve resulting from anchoring the valve stent by only using the barb structure or only through the inward recess on the transition tract structure can be reduced, i.e., preventing the natural mitral valve from bearing excessive force, reducing the risk of fatigue failure of the natural mitral valve, and improving the anchoring effect of the valve stent.

DESCRIPTION OF REFERENCE NUMERALS

101—mitral annulus; 102—mitral leaflet; 103—chordae tendineae; 104—papillary muscle;
200—valve stent;
210—inflow tract structure; 220—ring structure; 221—first end portion; 222—second end portion; 224—first wave rod; 225—first node; 230—lug; 231—third end portion; 232—fourth end portion;
240—transition tract structure; 241—fifth end portion; 242—sixth end portion; 244—second wave rod; 245—second node;
250—outflow tract structure; 251—seventh end portion; 252—eighth end portion; 254—third wave rod; 255—third node; 256—first section;
261—second barb; 262—first barb; 263—first fixation end; 264—first free end; 265—second fixation end; 266—second free end;
270—extension structure; 271—ninth end portion; 272—tenth end portion; 274—first connection end; 275—second connection end; 276—fourth node;
310—prosthetic leaflet; 320—suture skirt;
F1—first direction; δ1—first angle; F2—second direction; δ2—second angle.

DETAILED DESCRIPTION

Figure 1:
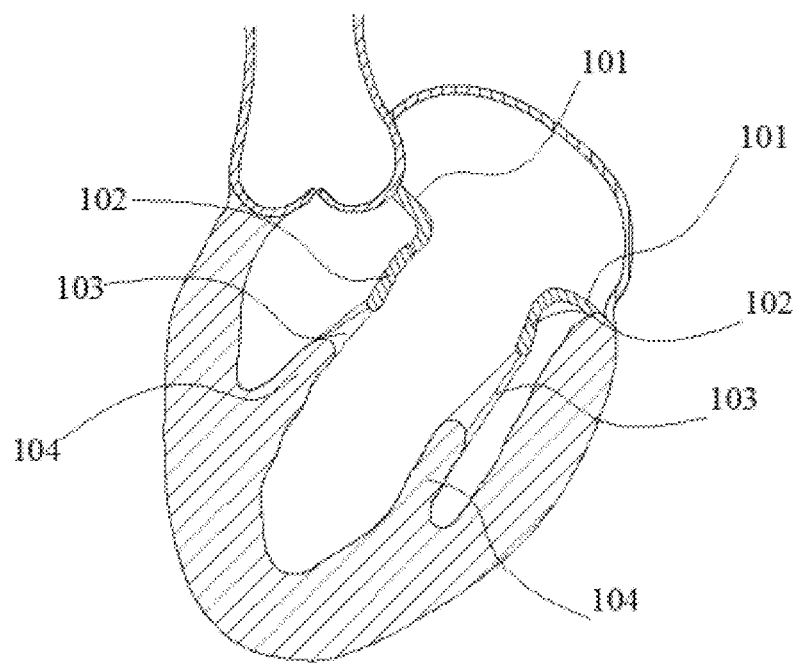
FIG. 1 is a sectional view of the left heart.

FIG. 1 is a sectional view of the left heart. Referring to FIG. 1, the natural mitral valve is located on the left ventricular outflow tract structure from the left atrium to the left ventricle, like a "one-way valve" disposed on the left ventricular inflow tract. The natural mitral valve includes mitral annuluses 101, mitral leaflets 102, chordae tendineaes 103, and papillary muscles 104. The papillary muscle 104 is attached to a myocardial wall, one end of the chordae tendineae 103 is connected to the papillary muscle 104, and the other end of the chordae tendineae 103 is connected to the mitral leaflet 102. Blood cannot flow from the left atrium to the left ventricle through the natural mitral valve when the natural mitral valve is closed. Blood flows from the left atrium to the left ventricle through the natural mitral valve when the natural mitral valve is open. A mitral valve prosthesis generally includes a mitral valve and a mitral stent. The mitral valve prosthesis is released in the natural mitral valve to replace the original natural mitral valve to achieve the "one-way valve" function. After implanted, the mitral valve prosthesis is anchored through the interference fit of the mitral stent to the mitral annulus 101 and the mitral leaflet 102. However, most patients with mitral regurgitation have a mitral valve calcified to a small extent, it is impossible to provide sufficient anchoring force through interference fit, resulting in unstable anchoring of the mitral valve prosthesis.

The tricuspid valve, as the atrioventricular valve of the right heart, has a structure similar to that of the mitral valve, and also includes leaflets, valvular annulus, chordae tendineae, and papillary muscles. The principle of the transcatheter mitral valve implantation is the same as that of the transcatheter tricuspid valve implantation. The principle of the mitral valve prosthesis can also be applied to the tricuspid valve prosthesis. In addition, the problem also occurs in tricuspid valve prosthesis, which is that most patients with tricuspid regurgitation have a tricuspid valve calcified to a small extent, it is impossible to provide sufficient anchoring force through interference fit, resulting in unstable anchoring of the tricuspid valve prosthesis.

On this basis, the inventors have proposed a valve stent and a valve prosthesis to improve the problem of unstable anchoring of the existing mitral stent, mitral valve prosthesis, tricuspid stent, and tricuspid valve prosthesis. In the present application, the natural valve includes a natural mitral valve and a natural tricuspid valve. The valve stent and the valve prosthesis proposed by the present application are further described in detail below with reference to the accompanying drawings and specific embodiments. It should be noted that the drawings are in a very simplified form and use non-precise proportions, and are only intended to conveniently and explicitly assist in describing the objectives of embodiments of the present application. The valve stent in the following embodiments is applicable to both the mitral stent and the tricuspid stent, and the valve prosthesis is applicable to both the mitral valve prosthesis and the tricuspid valve prosthesis. The mitral stent and the mitral valve prosthesis are taken as an example below for description.

As used herein, "outward" refers to an extension line that expands in a radial direction from the central axis of the valve stent which serves as a start point, and includes an extension line radially extending perpendicular to the central axis and an extension line radially expanding in non-right angle mode to the central axis, and "inward" refers to an extension line that expands in the radial direction towards the central axis of the valve stent which serves as an end point, and includes an extension line radially expanding perpendicular to the central axis and an extension line radially expanding in non-right angle mode to the central axis.

As used herein, a "proximal end" and a "distal end" are relative orientations, relative positions and directions of elements or actions relative to each other from the perspective of a surgeon using the medical instruments. Although the "proximal end" and the "distal end" are not restrictive, the "proximal end" generally refers to the end of the medical device that is close to the surgeon during normal operation, while the "distal end" generally refers to the end that first enters the patient.

In addition, the term "or" in the following embodiments is generally used as having the meaning including "and/or", unless otherwise explicitly stated.

Embodiment 1

Figure 2:
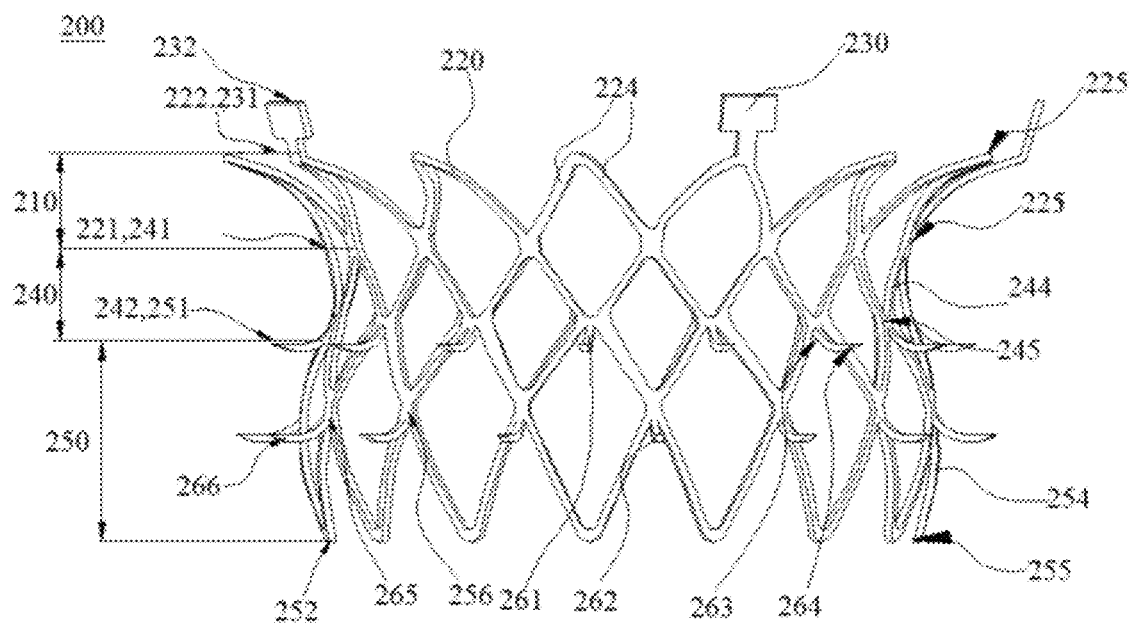
FIG. 2 is a schematic structural diagram of a valve stent in an expanded state according to Embodiment 1 of the present application.
Figure 3:
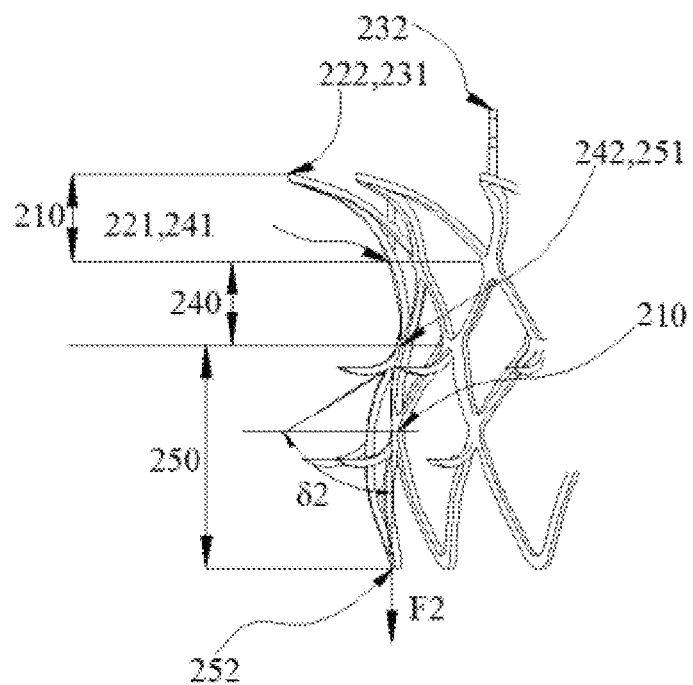
FIG. 3 is a schematic partial enlarged view of a valve stent in an expanded state according to Embodiment 1 of the present application.
Figure 26:
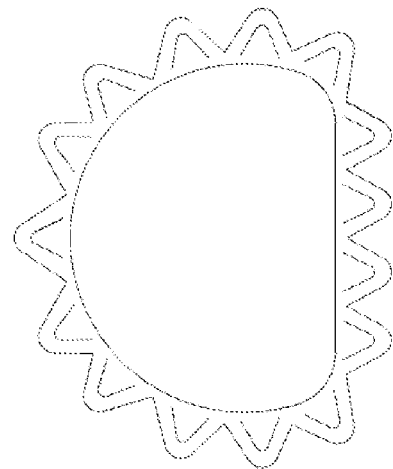
FIG. 26 is still another top view of a ring structure of the valve stent in an expanded state according to Embodiment 1 of the present application.
Figure 27:
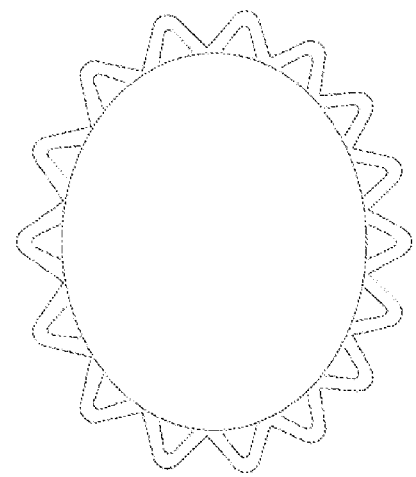
FIG. 27 is still another top view of a ring structure of the valve stent in an expanded state according to Embodiment 1 of the present application.

FIG. 2 is a schematic structural diagram of a valve stent in an expanded state according to Embodiment 1 of the present application. FIG. 3 is a schematic partial enlarged view of a valve stent in an expanded state according to Embodiment 1 of the present application. Referring to FIGS. 2 and 3, this embodiment provides a valve stent 200 which is a self-expanding stent. The valve stent 200 has a compressed state and an expanded state. The valve stent 200 has a central axis (not shown), and the radial sections of the valve stent are perpendicular to the central axis of the valve stent 200. In this embodiment, the central axis is a straight line. In other embodiments, the central axis may also be a curve. The valve stent 200 is in the shape of a mesh tube. Specifically, the radial sections of the valve stent 200 are distributed in a circular ring mode, and the sizes of the radial sections of the valve stent 200 gradually change along the central axis of the valve stent 200. In other embodiments, the radial sections of the valve stent 200 may also be distributed in other shapes, for example, distributed in a D-shaped ring or elliptical ring mode, as shown in FIGS. 26-27, and the sizes of the radial sections of the valve stent 200 change only along the central axis of the valve stent 200.

The valve stent 200 includes a mesh-shaped inflow tract structure 210, a mesh-shaped transition tract structure 240, a mesh-shaped outflow tract structure 250, and a barb structure. The inflow tract structure 210, the transition tract structure 240, and the outflow tract structure 250 are sequentially connected in the shape of a mesh tube. The transition tract structure 240 is located between the inflow tract structure 210 and the outflow tract structure 250. One end of the transition tract structure 240 is fixedly connected to the inflow tract structure 210, and the other end of the transition tract structure 240 is fixedly connected to the outflow tract structure 250. The barb structure is disposed on peripheral surfaces of the outflow tract structure 250 and the transition tract structure 240. Blood flows through the interiors of the inflow tract structure 210, the transition tract structure 240, and the outflow tract structure 250 sequentially after the valve stent 200 is released at the natural mitral valve. The inflow tract structure 210 includes a ring structure 220. The valve stent 200 further includes a plurality of lugs 230.

The ring structure 220 is in the shape of a mesh tube. The ring structure 220 has a first end portion 221 and a second end portion 222. The second end portion 222 is a free end.

In the expanded state, the diameter of the radial section of the first end portion 221 of the ring structure 220 is smaller than the diameter of the radial section of the second end portion 222 of the ring structure 220. That is, the first end portion 221 of the ring structure 220 is a small end, and the second end portion 222 of the ring structure 220 is a large end. The ring structure 220 transitions smoothly from the first end portion 221 to the second end portion 222. Preferably, the outer contour of the ring structure 220 fits to a left atrioventricular ostium, so as to facilitate positioning by means of the ring structure 220 during surgery. Specifically, the outer contour of the ring structure 220 fits to the annulus of the natural mitral valve of the left atrioventricular ostium.

Figure 4:
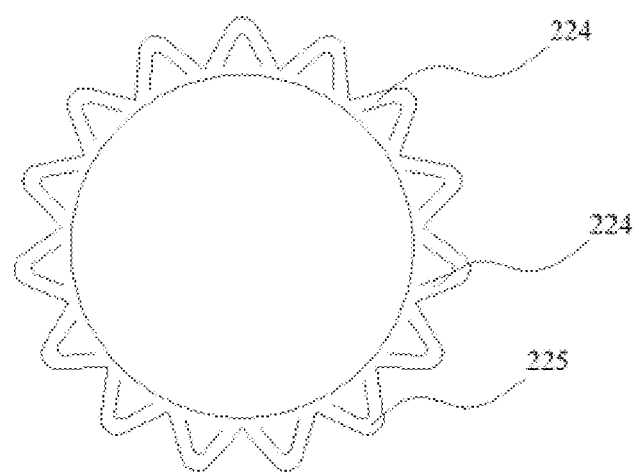
FIG. 4 is a top view of a ring structure of the valve stent in an expanded state according to Embodiment 1 of the present application.

In this embodiment, FIG. 4 is a top view of a ring structure of the valve stent in an expanded state according to Embodiment 1 of the present application. Referring to FIGS. 2 and 4, the ring structure 220 includes a group of first wave rod units (not shown). This group of first wave rod units includes a plurality of first wave rod units, and adjacent two of the first wave rod units are fixedly connected in sequence. The first wave rod unit is composed of two first wave rods 224, and the first wave rod unit is, for example, V-shaped. Every two adjacent first wave rods 224 extend from the first end portion 221 of the ring structure 220 to the second end portion 222 of the ring structure 220 and are intersected with each other. Two adjacent first wave rods 224 of adjacent two of the first wave rod units are fixedly connected at the first end portion 221 of the ring structure 220. A connection point where two first wave rods 224 in the first wave rod unit are connected to each other at the second end portion 222 is a first node 225.

Figure 7:
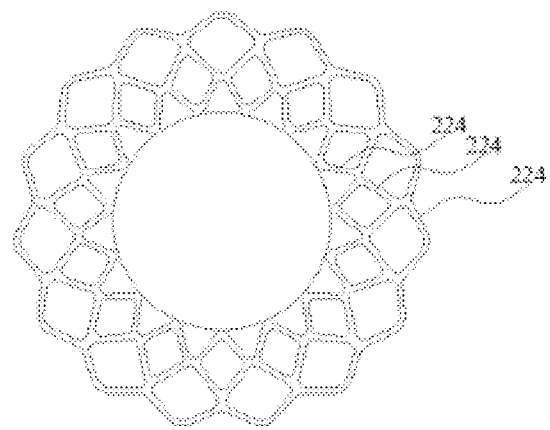
FIG. 7 is yet another top view of a ring structure of the valve stent in an expanded state according to Embodiment 1 of the present application.

In this embodiment, the ring structure 220 may include a plurality of groups of first wave rod units. The plurality of groups of first wave rod units are connected sequentially from the first end portion 221 of the ring structure 220 to the second end portion 222 of the ring structure 220. FIG. 7 is yet another top view of a ring structure of the valve stent in an expanded state according to Embodiment 1 of the present application. For example, referring to FIG. 7, the ring structure may include three groups of first wave rod units. For another example, the ring structure may include two groups, four groups, or five groups of first wave rod units. Adjacent two groups of first wave rod units are connected to each other by means of the first node of each group of first wave rod units to improve the strength of the ring structure and simplify the ring structure.

Figure 5:
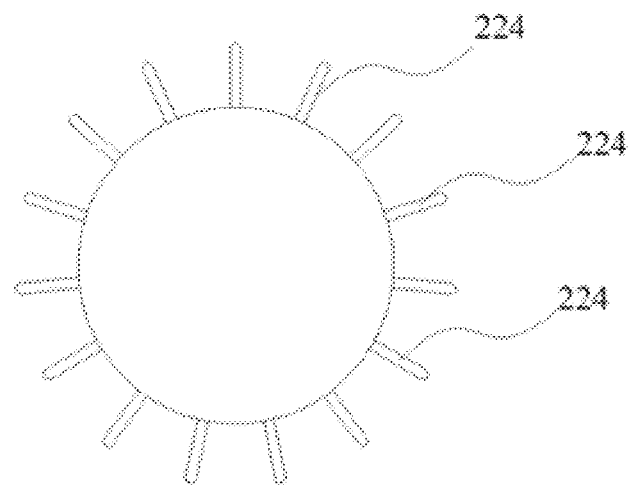
FIG. 5 is another top view of a ring structure of the valve stent in an expanded state according to Embodiment 1 of the present application.
Figure 6:
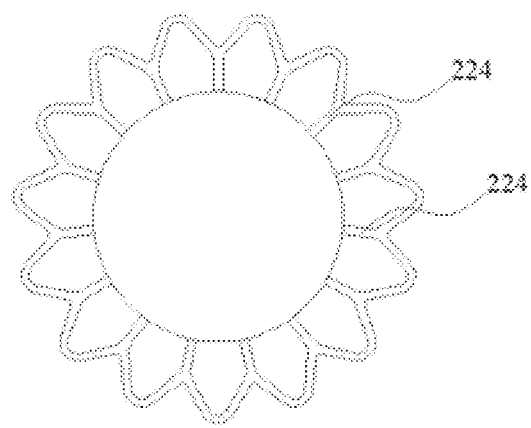
FIG. 6 is still another top view of a ring structure of the valve stent in an expanded state according to Embodiment 1 of the present application.

In this embodiment, the first wave rod unit may be triangular, U-shaped, diamond-shaped, pentagonal, or the like formed by a plurality of first wave rods. FIG. 6 is still another top view of a ring structure of the valve stent in an expanded state according to Embodiment 1 of the present application. For example, referring to FIG. 6, the first wave rod unit is pentagonal or the like. For another example, referring to FIG. 7, the first wave rod unit is V-shaped. For another example, FIG. 5 is another top view of a ring structure of the valve stent in an expanded state according to Embodiment 1 of the present application. Referring to FIG. 5, the first wave unit may even include only one rod-like first wave rod 224.

The diameter of the second end portion 222 of the ring structure 220 is greater than the maximum diameter of the atrioventricular ostium. The diameter of the ring structure 220 is preferably in a range of 30 mm to 70 mm, which can prevent the valve stent 200 from falling into the left ventricle during diastole.

Figure 8:
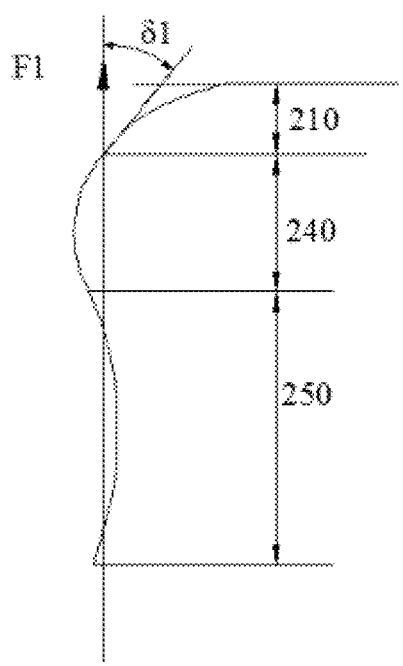
FIG. 8 is a schematic diagram of a contour of the valve stent in an expanded state according to Embodiment 1 of the present application.

FIG. 8 is a schematic diagram of a contour of the valve stent in an expanded state according to Embodiment 1 of the present application. Referring to FIG. 8, an angle between the ring structure 220 and the first direction F1 is a first angle δ1, and the first angle δ1 is at least 60° and at most 150°. The first direction F1 is a direction parallel to the central axis of the valve stent 200 and from the first end portion 221 to the second end portion 222 of the ring structure 220.

Preferably, the ring structure 220 may cover the left atrioventricular ostium.

Preferably, the second end portion 222 of the ring structure 220 may extend into the left atrium, and cover the atrioventricular ostium and part of an inner wall structure of the left atrium.

In this embodiment, the sizes of the first wave rod units of each group are consistent, that is, the ring structure 220 is a radially symmetrical circular ring. In other embodiments, the sizes of the first wave rod units of each group are inconsistent, so that the radial section of the ring structure 220 is in other shapes, such as a D-shaped ring or an elliptical ring.

Referring to FIG. 2, the lugs 230 are rectangular pieces. Certainly, in other embodiments, the lugs may be in other shapes, which is not limited in the present application. The lug 230 is fixedly connected to the ring structure 220. The lug 230 has a third end portion 231 and a fourth end portion 232. The third end portion 231 of the lug 230 is fixedly connected to the ring structure 220. The fourth end portion 232 is a free end. The lugs 230 are connected to a valve conveyor, and facilitate the delivery of the valve stent 200 into the natural mitral valve.

Preferably, referring to FIG. 2, the third end portion 231 of the lug 230 is fixedly connected to the second end portion 222 of the ring structure 220. Further, the third end portion 231 of the lug 230 is fixedly connected to the first node 225 on the second end portion 222 of the ring structure 220.

Preferably, the lug 230 extends from the third end portion 231 along the central axis of the valve stent 200 towards a direction away from the second end portion 222 of the ring structure 220.

Preferably, the lug is a metal sheet.

Preferably, the plurality of the lugs 230 is disposed parallel to the central axis of the valve stent. Referring to FIG. 2, the transition tract structure 240 is fixedly connected to the inflow tract structure 210. The transition tract structure 240 includes a fifth end portion 241, a sixth end portion 242, and a first middle section. The fifth end portion 241 is fixedly connected to the first end portion 221 of the ring structure 220. The six end portion 242 is located at an end away from the inflow tract structure 210, and the fifth end portion and the sixth end portion are located at two ends of the first middle section in the axial direction. Referring to FIG. 2, in the expanded state, the diameters of the radial sections of two end portions 241 and 242 of the transition tract structure 240 are greater than the diameter of the radial section of the first middle section, that is, the transition tract structure 240 is inwardly recessed. The transition tract structure 240 which is inwardly recessed, on the one hand, makes it possible for the annulus and leaflets of the natural mitral valve to fill into the recess, which facilitates anchoring the valve stent 200 on the natural mitral valve and, on the other hand, may match in shape with the annulus of the natural mitral valve, thereby facilitating the positioning of the valve stent 200 and the release of the valve stent 200 into the natural mitral valve by a surgeon. In addition, the recess is filled with the annulus and leaflets of the natural mitral valve, so that the valve stent 200 is better covered by the annulus and leaflets of the natural mitral valve, thereby avoiding the blood flowing from the left atrium into the left ventricle through a gap between the natural mitral valve and the valve stent 200.

Further, the transition tract structure 240 and the ring structure together form an inward recess. In addition, the diameter of the second end portion 222 of the ring structure is greater than the diameter of the first end portion 221 of the ring structure. The ring structure extends the radial depth of the recess of the transition tract structure 240, and increases the length of the recess along the direction of the central axis, so that more portions of the natural mitral valves are filled into the recess, which provides more radial support force for the anchoring of the valve stent. Moreover, the inward recess formed by the transition tract structure 240 and the ring structure may match in shape with the annulus of the natural mitral valve, further facilitating the release of the valve stent 200 into the natural mitral valve by the surgeon.

In this embodiment, the transition tract structure 240 includes only one group of second wave rod units. Each of the second wave rod units is composed of two second wave rods 244, and the second wave rod unit is each V-shaped. Every two adjacent second wave rods 244 extend towards the fifth end portion 241 from a position close to the sixth end portion 242 and are intersected with each other. Two adjacent second wave rods 244 of adjacent two of second wave rod units are fixedly connected at the position close to the sixth end portion 242. The second wave rods 244 connected to each other in each group of second wave rod units form a second node 245. The first node 225 of the inflow tract structure 210 and the second node 245 of the transition tract structure 240 are connected to each other to improve the strength of the transition tract structure 240 and simplify the transition tract structure 240.

In other embodiments, the transition tract structure may include a plurality of groups of second wave rod units. The plurality of groups of second wave rod units is connected sequentially along the central axis of the valve stent. Each group of second wave rod units includes a plurality of second wave rod units, and adjacent two of the second wave rod units are fixedly connected in sequence. The second wave rod unit may be triangular, U-shaped, diamond-shaped, pentagonal, or the like formed by a plurality of second wave rods. Adjacent two groups of second wave rod units are preferably connected to each other by means of a second node of each group of second wave rod units.

Preferably, in this embodiment, in the expanded state, the diameter of the radial section of the transition tract structure 240 is greater than the diameter of the annulus of the natural mitral valve. Further, the diameter of each radial section of the transition tract structure 240 is in a range of 25 mm to 55 mm.

In the expanded state, the length of the inward recess of the transition tract structure 240 along the central axis of the valve stent 200 is selected from a range from 2 mm to 20 mm.

Referring to FIG. 2, the outflow tract structure 250 is fixedly connected to the transition tract structure 240. The outflow tract structure 250 has a seventh end portion 251, an eighth end portion 252, and a second middle section. The seventh end portion 251 of the outflow tract structure 250 is fixedly connected to the sixth end portion 242 of the transition tract structure 240. The eighth end portion 252 is located at the end away from the transition tract structure 240, and the eighth end portion 252 is a free end. The seventh end portion 251 and the eighth end portion 252 are located at two ends of the second middle section in the axial direction.

Still referring to FIGS. 2 and 8, in this embodiment, in the expanded state, the contour of the peripheral surface of the outflow tract structure 250 has a shape protruding towards the outside of the outflow tract structure 250. That is, the diameter of the radial section of the seventh end portion 251 and the diameter of the radial section of the eighth end portion 252 are smaller than the diameter of the radial section of the second middle section. The section with the maximum diameter among the radial sections of the outflow tract structure 250 is a first section 256. The contours of the peripheral surfaces of the transition tract structure 240 and the outflow tract structure 250 are S-shaped.

Figure 9:
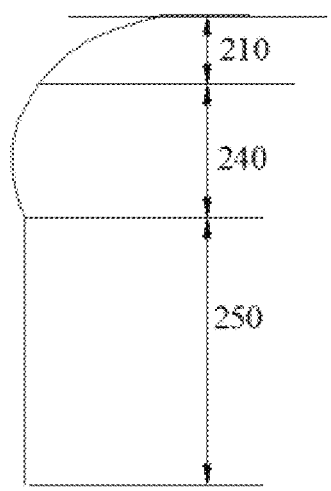
FIG. 9 is a schematic diagram of another contour of the valve stent in an expanded state according to Embodiment 1 of the present application.
Figure 10:
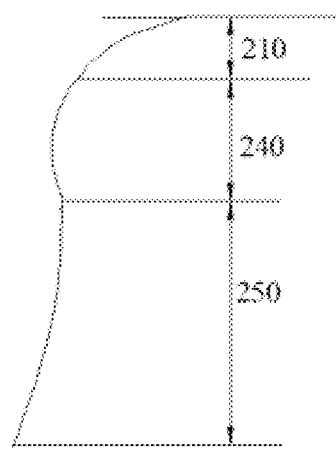
FIG. 10 is a schematic diagram of still another contour of the valve stent in an expanded state according to Embodiment 1 of the present application.

In this embodiment, the diameter of each radial section of the outflow tract structure 250 may also be other cases. For example, in the expanded state, the diameter of each radial section of the outflow tract structure is preferably greater than the diameter of the radial section of the seventh end portion 251. That is, the diameter of the radial section of the seventh end portion 251 is the minimum diameter of each radial section of the outflow tract structure 250, and the outflow tract structure 250 has an outwardly expanding shape from the seventh end portion 251 to the eighth end portion 252. Alternatively, referring to FIG. 9, which is a schematic diagram of another contour of the valve stent in an expanded state according to Embodiment 1 of the present application. The diameters of the radial sections of the outflow tract structure 250 are equal, and the transition tract structure 240 is cylindrical. Alternatively, referring to FIG. 10, which is a schematic diagram of still another contour of the valve stent in an expanded state according to Embodiment 1 of the present application. The diameter of each radial section of the outflow tract structure 250 is smaller than the diameter of the radial section of the seventh end portion 251. Alternatively, the diameter of the radial section of the outflow tract structure 250 may be changed in other ways. For example, the diameter of the radial section of the outflow tract structure 250 away from the seventh end portion 251 is greater than the diameter of the radial section of the seventh end portion 251, and the diameter of the radial section of the outflow tract structure 250 close to the seventh end portion 251 is smaller than the diameter of the radial section of the seventh end portion 251.

In this embodiment, referring to FIG. 2, the outflow tract structure 250 includes only one group of third wave rod units. Each of the third wave rod units is composed of four third wave rods 254, and each third wave rod unit is diamond-shaped. Four sides of the third wave rod unit correspond to the four third wave rods 254, respectively. The third wave rod unit has four vertices. One vertex of the third wave rod unit is located on the eighth end portion 252, and another vertex opposite to the vertex located on the eighth end portion 252 is located on the seventh end portion 251. The other two vertices of the third wave rod unit are fixedly connected to the vertices of other two third wave rod units adjacent to the third wave rod unit, respectively. The other two vertices of the third wave rod unit are preferably located on the first section 256. The vertex of the third wave rod unit located on the eighth end portion 252 and the vertex located on the seventh end portion 251 are referred to as a third node 255. The second node 245 on the transition tract structure 240 is connected to the third node 255 of the outflow tract structure 250 on the seventh end portion 251 to increase the strength of the outflow tract structure 250 and simplify the structure of the outflow tract structure 250.

In other embodiments, the outflow tract structure 250 may include a plurality of groups of third wave rod units. The plurality of groups of third wave rod units is connected sequentially along the central axis of the valve stent 200. Adjacent two groups of third wave rod units are preferably connected to each other by means of connection points formed by connecting two or more third wave rods 254 on two ends of each group of third wave rod units to improve the strength of the outflow tract structure 250 and simplify the structure of the outflow tract structure 250. Each group of third wave rod units includes a plurality of third wave rod units, and every two adjacent third wave rod units are sequentially fixedly connected in a ring shape, such as a D-shaped ring, an elliptical ring or a circular ring. The third wave rod unit may be triangular, U-shaped, V-shaped, quadrangular, pentagonal or the like formed by a plurality of third wave rods.

The diameter of each radial section of the outflow tract structure 250 is in a range of 26 mm to 60 mm.

In other embodiments, the lugs 230 may also be disposed on the outflow tract structure, for example, on the eighth end portion 252 of the outflow tract structure. The third end portion 231 of the lug 230 is fixedly connected to the eighth end portion 252, and the fourth end portion 231 of the lug extends in a direction away from the outflow tract structure 250.

Referring to FIG. 2, the valve stent 200 further includes a barb structure, including a plurality of second barbs 261 and a plurality of first barbs 262. The second barb 261 has a first fixation end 263, and the first barb 262 has a second fixation end 265. One end of the second barb 261 away from the first fixation end 263 is a first free end 264, and one end of the first barb 262 away from the second fixation end 265 is a second free end 266. The first fixation ends 263 of all the second barbs 261 are disposed on the transition tract structure 240, and all of the second barbs 261 protrude from the first fixation ends 263 towards the outside of the transition tract structure 240. The second fixation ends 265 of the plurality of first barbs 262 are disposed on the outflow tract structure 250, and all the first barbs 262 protrude from the second fixation ends 265 towards the outside of the outflow tract structure 250.

The plurality of the second barbs 261 and the plurality of first barbs 262 pierce into the leaflets and annulus tissues of a natural valve to anchor the valve stent 200 on the natural valve after the valve stent 200 is implanted into the heart. The valve stent 200 is anchored to the natural mitral valve by means of the barb structure and the inward recess formed by the transition tract structure 240 and the ring structure, which can improve the anchoring effect of the valve stent 200, and meanwhile, the influence on the natural mitral valve resulting from anchoring the valve stent 200 by only using the barb structure or only through the inward recess formed by the transition tract structure 240 and the ring structure can be reduced, i.e., avoiding the natural mitral valve from bearing excessive force and reducing the risk of fatigue failure of the natural mitral valve.

In this embodiment, the first fixation ends 263 of all the second barbs 261 are preferably located at a position where the transition tract structure 240 and the outflow tract structure 250 are connected. That is, the first fixation ends 263 of all the second barbs 261 are disposed on the sixth end portion 242 of the transition tract structure 240 or on the seventh end portion 251 of the outflow tract structure 250. The second fixation ends 265 of all the first barbs 262 are disposed on the outflow tract structure 250. In addition, all the second barbs 261 extend in a direction close to the outflow tract structure 250.

The second barbs 261 extend towards a position close to the free end of the outflow tract structure 250 from a position where the transition tract structure 240 and the outflow tract structure 250 are connected, and protrude outwards from the valve stent 200. The second barbs 261 make the inward recess formed by the transition tract structure 240 and the ring structure to be recessed more in the radial section, and to be extended more greatly in length in the axial section, so that more annulus and leaflets of the natural mitral valve can be filled into the recessed shape, thereby making the valve stent 200 to be anchored stably. In addition, the second barbs 261 and the inward recess which is formed by the transition tract structure 240 and the ring structure and recessed inwards the valve stent 200 can facilitate the positioning of the valve stent 200 and facilitate the release of the valve stent 200 into the natural mitral valve by the surgeon.

Specifically, during implementation of the valve stent 200, the natural structure of the heart is used as a guide to determine the position where the valve stent 200 is released. The inward recess of the transition tract structure 240 can be matched with the annulus of the natural mitral valve, which facilitates the positioning of the valve stent 200. Moreover, the second barbs 261 increase an area of the inward recess which is formed by the transition tract structure 240 and the ring structure and recessed inwards the valve stent 200, so that the area of the valve stent 200 matching with the annulus of the natural mitral valve is increased, which reduces the difficulty in positioning the valve stent 200 when released, and increases the adjustable length of the valve stent 200 along the central axis when the valve stent 200 is positioned, thereby further reducing the difficulty in surgeon's operation.

Certainly, in other embodiments, the plurality of second barbs 261 may be distributed on the transition tract structure 240 in other ways. For example, a part of the second barbs 261 is distributed between the fifth end portion 241 and the sixth end portion 242 of the transition tract structure 240, and the other part of the second barbs 261 is distributed on the sixth end portion 242 of the transition tract structure 240. For another example, the first fixation ends 263 of all the second barbs 261 are disposed between the fifth end portion 241 and the sixth end portion 242 of the transition tract structure 240.

In this embodiment, the second fixation ends 265 of all the first barbs 262 are disposed on the first section 256. The plurality of first barbs 262 extends towards a position close to the eighth end portion 252 of the outflow tract structure 250 from the second fixation end 265. The first barbs 262 are disposed on the first section 256 and the outflow tract structure 250 protrudes outwards, and the first barbs 262 extend towards a position close to the eighth end portion 252 of the outflow tract structure 250 from the second fixation end 265. Therefore, the first barbs 262 make the inward recess which is formed by the outflow tract structure 250 and the transition tract structure 240 and recessed inwards the valve stent 200 to be recessed more in the radial section, and to extend more greatly in length in the axial section, so that more annulus and leaflets of the natural mitral valve can be filled into the recessed shape, thereby making the valve stent 200 to be anchored stably. In addition, the first barbs 262, the outflow tract structure 250 and the inward recess which is formed by the transition tract structure 240 and the ring structure and recessed inwards the valve stent 200 can facilitate the positioning of the valve stent 200 and facilitate the release of the valve stent 200 into the natural mitral valve by surgeon. The first barbs 262, the outflow tract structure 250 and the inward recess which is formed by the transition tract structure 240 and the ring structure and recessed inwards the valve stent 200 increase the recessed area, so that the area of the valve stent 200 matching with the annulus of the natural mitral valve is increased, which further reduces the difficulty in positioning the valve stent 200 when released, and increases the adjustable length of the valve stent 200 along the central axis when the valve stent 200 is positioned, thereby further reducing the difficulty in surgeon's operation. In this embodiment, referring to FIG. 3, an angle between tangents of the first fixation end 263 of the second barb 261 and the second fixation end 265 of the first barb 262 and the second direction F2 is a second angle δ2. The second angle δ2 is at least 10° and at most 150°. The second direction F2 is a direction, in parallel to the central axis of the valve stent 200, in the axial section of the valve stent 200, from the transition tract structure 240 to the outflow tract structure 250.

In other embodiments, the extension direction of the second barbs 261 and the first barbs 262 may also be in other ways. For example, the plurality of second barbs 261 extends towards a position close to the eighth end portion 252 of the outflow tract structure 250, and the plurality of first barbs 262 extend towards a position close to the seventh end portion 251 of the outflow tract structure 250.

In this embodiment, the second barbs 261 and the first barbs 262 have the same shape and the same size. In other embodiments, the sizes of the second barbs 261 and the first barbs 262 may be same or not, and the shapes may be same or not. For example, the second barbs 261 distributed on the transition tract structure 240 are the same in shape, the second barbs 261 distributed between two ends of the transition tract structure 240 is smaller than the second barbs 261 distributed at the other end of the transition tract structure 240, and the size and shape of the first barbs 262 are the same as those of the second barbs 261 distributed at the other end of the transition tract structure 240. For another example, the second barbs 261 and the first barbs 262 have the same shape and the same size. For yet another example, the second barbs 261 have shapes and sizes both different from those of the first barbs 262.

In this embodiment, the second barbs 261 and the first barbs 262 are preferably distributed on the transition tract structure 240 and the outflow tract structure 250 uniformly, so that the second barbs 261 and the first barbs 262 uniformly pierce into the leaflets and annulus tissues of the natural valve, the anchoring force exerted by the natural valve on the valve stent 200 is uniform, the valve stent 200 is anchored stably, and the force applied by the valve stent 200 on the natural valve is also relatively uniform, thereby reducing the damage to the natural valve caused by the second barbs 261 and the first barbs 262. In other embodiments, the second barbs 261 and the first barbs 262 may be distributed on the transition tract structure 240 and the outflow tract structure 250 in a non-uniform manner. For example, the intervals between the plurality of second barbs 261 on the seventh end portion 251 of the outflow tract structure 250 are not equal. In other embodiments, the first barbs may be disposed on the outflow tract structure in other ways. For example, the first barbs may be disposed at a third node of the outflow tract structure, and the number and positions of the first barbs are not limited.

As shown in FIG. 2, a row of second barbs is disposed on the transition tract structure, and a row of first barbs is disposed on the outflow tract structure, so as to prevent the barb structures from moving along the valve prosthesis after piercing into the natural valve, thereby improving the anchoring stability of the valve prosthesis.

In this embodiment, the length of the barb 261 from the first fixation end 263 to the first free end 264 is in a range of 0.5 mm to 8 mm, and the length of the first barb 262 from the second fixation end 265 to the second free end 266 is in a range of 0.5 mm to 8 mm.

In this embodiment, the first fixation end 263 of the second barb 261 is fixedly connected to the second node 245, and the second fixation end 265 of the first barb 262 is fixedly connected to the vertices of the third wave rod unit on the first section 256. In other embodiments, the second barbs 261 may be connected to other portions of the transition tract structure 240, and the first barbs 262 may also be connected to other portions of the transition tract structure 240 and the outflow tract structure 250.

Further, the first free end 264 of the first second barb 261 and the second free end 266 of the first barb 262 are both triangle-shaped or tapered and other shapes that are easy to pierce into the natural valve.

In this embodiment, the first fixation end 263 and the first free end 264 of the second barb 261 are in smooth transition, and the second fixation end 265 and the second free end 266 of the first barb 262 are in smooth transition. In this embodiment, the second barb 261 and the first barb 262 are an arc or a combination of multiple arcs, and the starting points of the arcs are located at the first fixation end 263 of the second barb 261 and the second fixation end 265 of the first barb 262, respectively. In other embodiments, the second barb 261 and the first barb 262 are a combination of arcs and straight lines, and the starting points of the arcs are located at the first fixation end 263 of the second barb 261 and the second fixation end 265 of the first barb 262, respectively. The first free end 264 of the second barb 261 and the second free end 266 of the first barb 262 are all straight lines, and the arc is tangent to the straight line. In this embodiment, the barb structure may include only the second barb or only the first barb.

The sum of the lengths of the outflow tract structure 250 and the transition tract structure 240 along the central axis is preferably in a range of 10 mm to 30 mm, to minimize the influence of the valve stent 200 on the structure of the natural mitral valve, which can reduce the risks of left ventricular reconstruction and blockage of the outflow tract structure of the left ventricle. The length of the valve stent 200 along the central axis is in a range of 10 mm to 60 mm.

The valve stent 200 may be made of nickel-titanium alloy or other biocompatible materials with memory characteristics.

In this embodiment, the valve stent 200 can be released into the heart through the left atrial approach, or can be released into the heart through the apical approach. The difference between the release of the valve stent 200 into the heart through the left atrial approach and the release of the valve stent 200 into the heart through the apical approach is that the release sequence of the valve stent 200 is different. During the release of the valve stent 200 into the heart through the left atrial approach, the outflow tract structure 250 is first released from the sheath. During the release of the valve stent 200 into the heart through the apical approach, the inflow tract structure 210 is first released from the sheath. In the following, taking the release of the valve stent 200 into the heart through the left atrial approach as an example, the process of releasing the valve stent 200 into the natural mitral valve by a delivery system is explained.

First, the valve stent 200 is compressed into the sheath of the delivery system from the proximal end of the sheath. In this case, the valve stent 200 is separated from the natural mitral valve.

Secondly, the valve stent 200 is pushed to the distal end of the sheath by means of a pusher of the delivery system, and the valve stent 200 is released at the distal end of the sheath.

During the release of the valve stent 200 at the distal end of the sheath, the outflow tract structure 250 and the transition tract structure 240 of the valve stent 200 are sequentially released from the sheath. The part of the valve stent 200 released from the sheath is automatically expanded and appears to be a conical structure.

Figure 11:
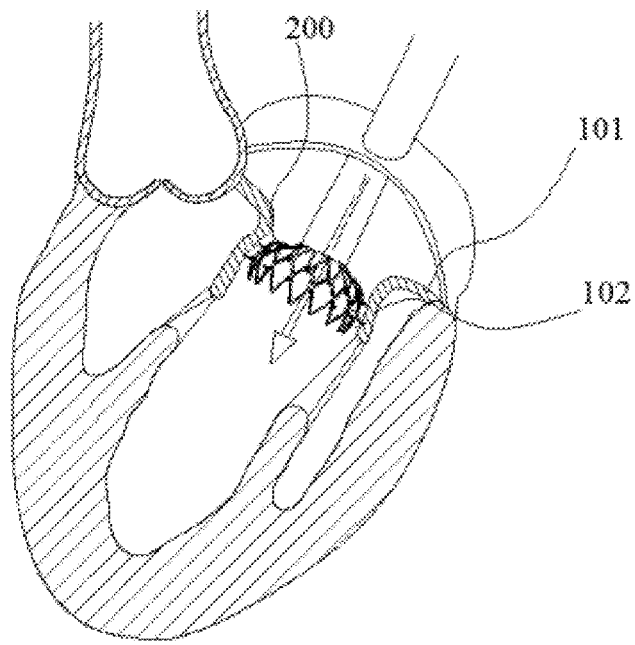
FIG. 11 is a schematic diagram showing release of a part of the valve stent from a sheath according to Embodiment 1 of the present application.

The valve stent 200 is continuously released. FIG. 11 is a schematic diagram showing release of a part of the valve stent from a sheath according to Embodiment 1 of the present application. Referring to FIG. 11, the barb structure begins to pierce into the leaflets and annulus of the natural mitral valve. In this case, the valve stent 200 can still be retrieved as a whole into the sheath.

The valve stent 200 is continuously released, until the inflow tract structure 210 of the valve stent 200 is completely released from the sheath.

Figure 12:
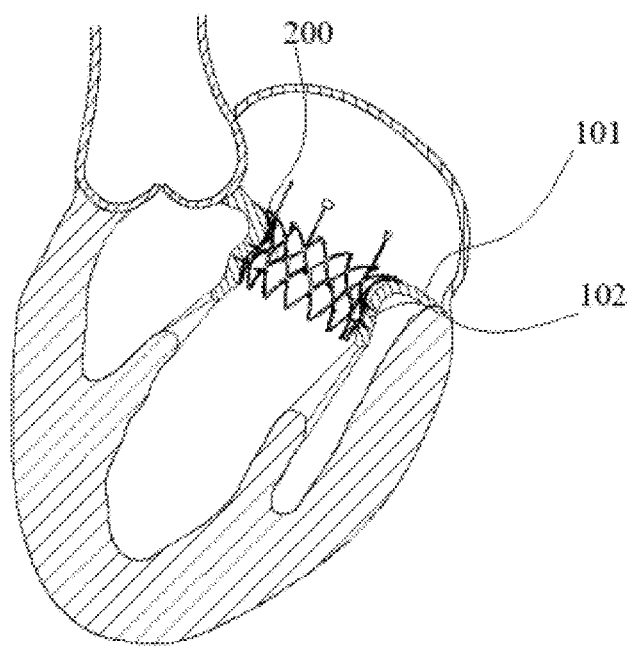
FIG. 12 is a schematic diagram showing that a valve stent is completely released from a sheath and anchored in a natural mitral valve according to Embodiment 1 of the present application.

Specifically, referring to FIG. 12, FIG. 12 is a schematic diagram showing that a valve stent 200 is completely released from a sheath and anchored in a natural mitral valve according to Embodiment 1 of the present application. When the valve stent 200 is released into the natural mitral valve, the valve stent 200 expands. In this case, the barb structure is anchored on the leaflets and annulus of the natural mitral valve. Under the compression of the valve stent 200, the annulus and leaflets of the natural mitral valve fill into the inward recess of the transition tract structure 240, and cover the peripheral surface of the transition tract structure 240. The ring structure 220 of the inflow tract structure 210 may cover the annulus of the natural mitral valve.

Embodiment 2

Figure 13:
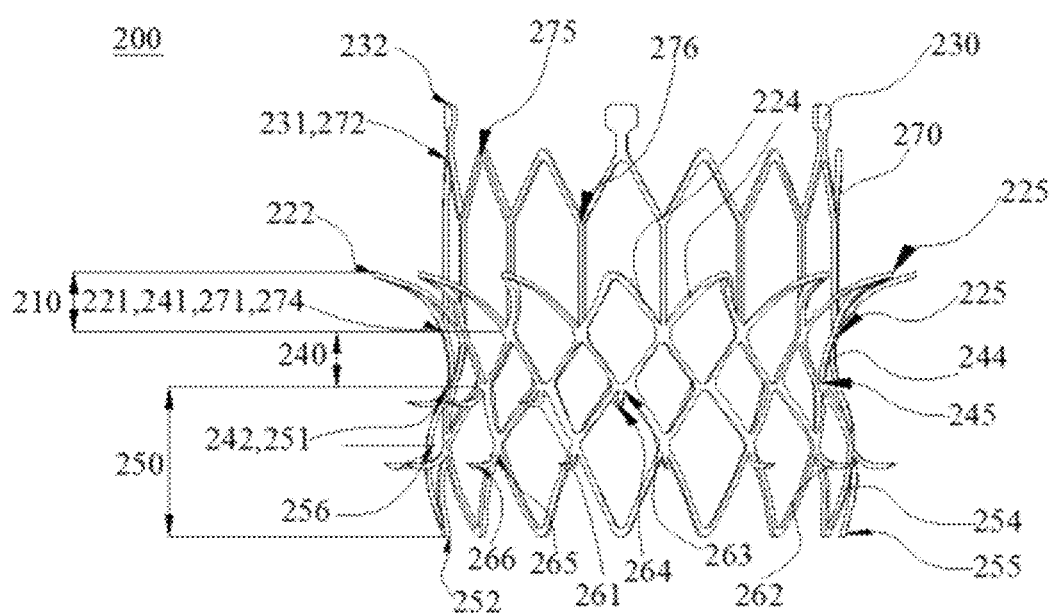
FIG. 13 is a schematic structural diagram of a valve stent in an expanded state according to Embodiment 2 of the present application.
Figure 14:
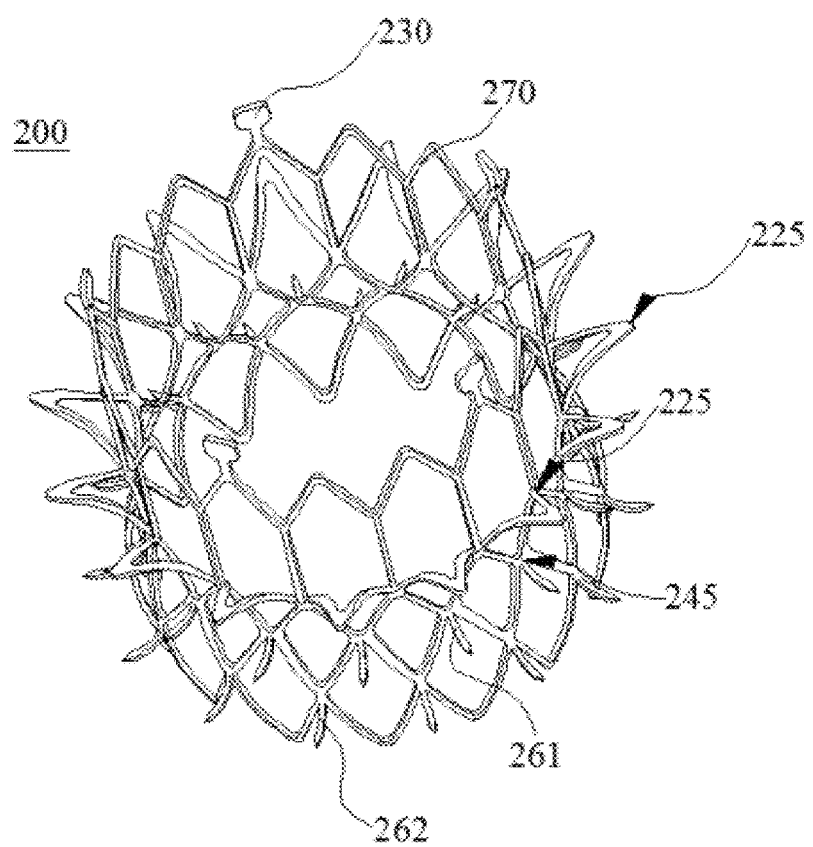
FIG. 14 is a schematic perspective view of a valve stent according to Embodiment 2 of the present application.

FIG. 13 is a schematic structural diagram of a valve stent in an expanded state according to Embodiment 2 of the present application. FIG. 14 is a schematic perspective view of a valve stent according to Embodiment 2 of the present application. Referring to FIGS. 13 and 14, the difference between the valve stent in this embodiment and the valve stent in Embodiment 1 is that the valve stent 200 in this embodiment further includes an extension structure 270 in the shape of a mesh tube, and the lug 230 is not directly connected to the ring structure 220, but is connected to the ring structure 220 by means of the extension structure 270.

In this embodiment, the extension structure is fixedly connected to the ring structure. The extension structure 270 has a ninth end portion 271 and a tenth end portion 272. The ninth end portion 271 is fixedly connected to the ring structure 220, and the tenth end portion 272 is away from the ring structure 220 and the transition tract structure 240. The lug 230 is fixedly connected to the extension structure 270. By providing the extension structure 270, the length of the valve stent 200 along the central axis can be increased, and thus the radial deformation of the valve stent 200 in the release process can be reduced, thereby preventing the valve stent 200 from moving along the central axis and thus improving the release stability of the valve stent 200. In addition, by providing the extension structure 270, the rigidity of the valve stent 200 when compressed is improved.

In this embodiment, the length of the extension structure 270 along the central axis is greater than the length of the ring structure 220 along the central axis when the valve stent 200 is compressed. Therefore, the extension structure 270 and the lug 230 are not released from the sheath when the ring structure 220, the transition tract structure 240, and the outflow tract structure 250 are released from the sheath. Therefore, the problem that due to expansion, the sizes of the ring structure 220, the transition tract structure 240, and the outflow tract structure 250 are increased in the radial direction and decreased in the central axis direction to cause the valve stent 200 to move axially can be further avoided. In addition, in the release process of the valve stent 200, since the extension structure 270 and the lug 230 are finally released from the sheath, the valve stent 200 is anchored to the natural mitral valve when the extension structure 270 and the lug 230 are released. Therefore, the axial impact received by the valve stent 200 is reduced when the extension structure 270 and the lug 230 are released, and thus, the release stability is further improved.

Figure 15:
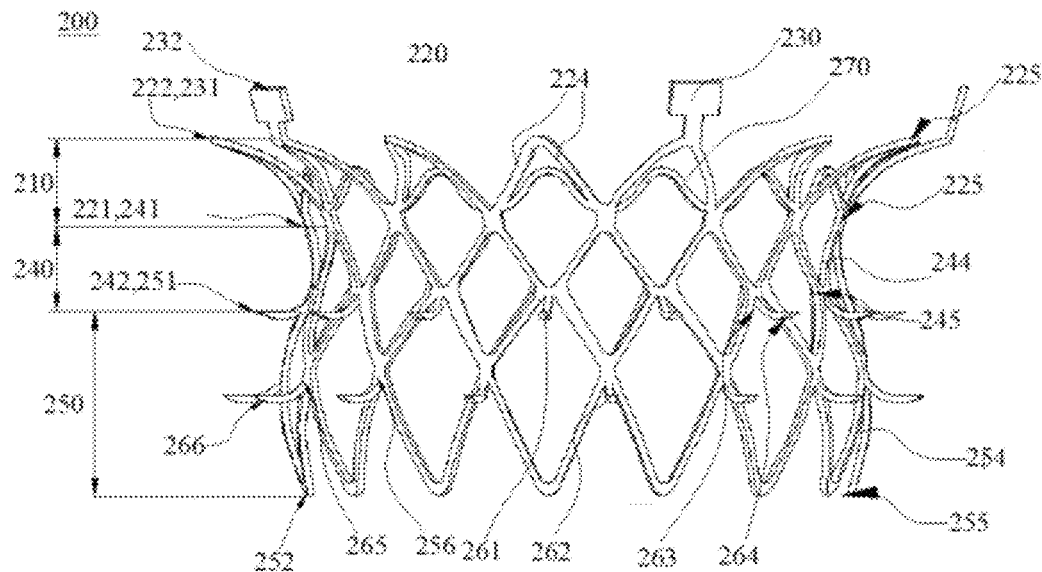
FIG. 15 is a schematic diagram of another valve stent in an expanded state according to Embodiment 2 of the present application.
Figure 16:
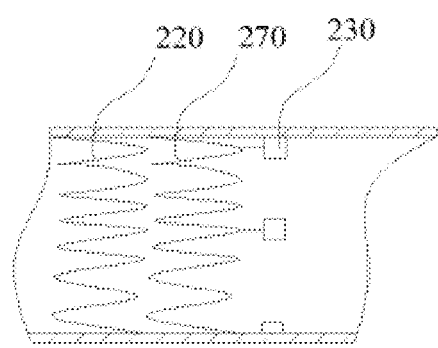
FIG. 16 is a partial schematic view showing that a valve stent is compressed in a sheath according to Embodiment 2 of the present application.
Figure 24:
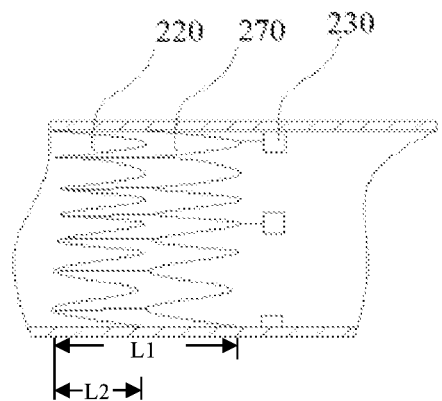
FIG. 24 is a partial schematic view showing that a valve stent is compressed in a sheath according to Embodiment 2 of the present application.
Figure 25:
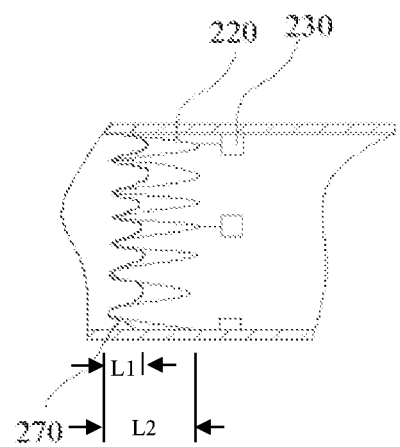
FIG. 25 is a partial schematic view showing that a valve stent is compressed in a sheath according to Embodiment 2 of the present application.

In this embodiment, the axial heights of the ring structure and the extension structure 270 may be inconsistent after being compressed. The axial length L1 of the extension structure may be greater than the axial length L2 of the ring structure, as shown in FIG. 24, or the axial length L2 of the ring structure may be greater than the axial length L1 of the extension structure 270, as shown in FIG. 25. For example, referring to FIG. 15, which is a schematic diagram of another valve stent in an expanded state according to Embodiment 2 of the present application. The lug is connected to the distal end of the ring structure when the outflow tract structure of the valve stent is released first and then the inflow tract structure is released, and the length of the ring structure which is compressed is greater than that of the extension structure. By providing the extension structure, the rigidity of the valve stent 200 after being compressed can be increased, and the release stability of the valve stent 200 can also be improved. Specifically, since the outflow tract structure and the transition tract structure of valve stent are released first, and then the inflow tract structure and the extension structure are released, as the extension structure is gradually released, the diameter of the extension structure gradually increases, and the shapes of the extension structure, the transition tract structure, and the outflow tract structure further approach their expanded shapes, so that the amount of morphological change of the extension structure, the transition tract structure, and the outflow tract structure after the valve stent is completely released can be reduced, thereby improving the release stability. In this embodiment, preferably, the extension structure 270 and the ring structure 220 are axially staggered on the peripheral surface of the valve stent. That is, in the compressed state, the extension structure 270 and the ring structure 220 are in contact with each other only at a connection point thereof, and do not overlap in the radial direction. FIG. 16 is a partial schematic view showing that a valve stent is compressed in a sheath according to Embodiment 2 of the present application. Referring to FIG. 16, the extension structure 270 and the ring structure 220 are distributed in a staggered manner after the valve stent 200 is compressed in the sheath, thereby preventing the extension structure 270 from causing increase in the diameter of the valve stent 200 after being compressed.

In this embodiment, the maximum diameter of the radial sections of the extension structure 270 is smaller than the maximum diameter of the radial sections of the ring structure, which can prevent the extension structure 270 from hindering the ring structure 220 from covering the annulus of the natural mitral valve, and can prevent the extension structure 270 from hindering the valve stent 200 from being positioned when the valve stent 200 is released.

In this embodiment, referring to FIGS. 13 and 14, the ninth end portion 271 of the extension structure 270 is preferably fixedly connected to the first end portion 221 of the ring structure 220.

In this embodiment, referring to FIGS. 13 and 14, the extension structure 270 includes a group of fourth wave rod units. The fourth wave rod unit includes a Y-shaped fourth wave rod. Each of the fourth wave rods has a first connection end 274 and two second connection ends 275. The first connection end 274 is preferably fixedly connected to the first end portion 221 of the ring structure 220. Two adjacent second connection ends 275 of adjacent two fourth wave rod units are fixedly connected. Two second connection ends 275 are preferably disposed symmetrically. A trifurcate intersection of the Y-shaped fourth wave rod included in each fourth wave rod unit of each group of fourth wave rod units forms a fourth node 276.

In other embodiments, the extension structure 270 may include a plurality of groups of fourth wave rod units. The plurality of groups of fourth wave rod units are connected sequentially from the ninth end portion 271 of the extension structure 270 to the tenth end portion 272 of the extension structure 270. Each group of fourth wave rod units includes a plurality of fourth wave rod units, and two adjacent fourth wave rod units are fixedly connected in sequence. Adjacent two groups of fourth wave rod units are preferably connected to each other by means of fourth nodes 276 of each group of fourth wave rod units to increase the strength of the ring structure 220 and simplify the ring structure 220, and not the first connection end 274 of each fourth wave rod is connected to one fourth node 276.

For example, the extension structure 270 may include three groups of fourth wave rod units. For another example, the extension structure 270 may include two groups, four groups, or five groups of fourth wave rod units.

Figure 17:
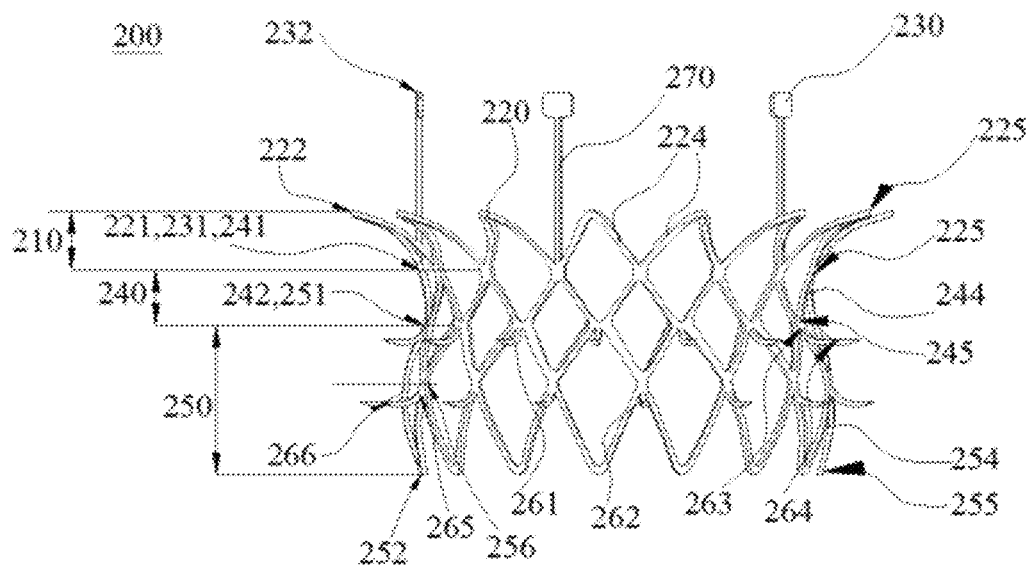
FIG. 17 is a schematic structural diagram of still another valve stent in an expanded state according to Embodiment 2 of the present application.

In other embodiments, the fourth wave rod unit may be triangular, U-shaped, diamond-shaped, pentagonal, or the like formed by a plurality of fourth wave rods. Alternatively, referring to FIG. 17, which is a schematic structural diagram of still another valve stent in an expanded state according to Embodiment 2 of the present application. The fourth wave rod unit may include only one rod-like fourth wave rod.

In this embodiment, the extension structure 270 is integrally formed. In other embodiments, the extension structure 270 may be formed by connecting a plurality of fourth wave rod units through other processing methods. For example, the fourth wave rod units may be fixedly connected by welding.

In this embodiment, the extension structure 270 and the ring structure 220 are integrally formed. In other embodiments, the extension structure 270 and the ring structure 220 are connected through a rigid connection method such as welding or riveting, or are connected through a flexible connection method such as knitting.

The length of the extension structure 270 along the central axis of the valve stent 200 may be in a range of 1 mm to 25 mm.

In this embodiment, the third end portion 231 of the lug 230 is preferably fixedly connected to a point of the extension structure 270 located on the tenth end portion 272, and the fourth end portion 232 of the lug is a free end.

The lugs 230 extend towards a position close to the second end portion 222 of the ring structure 220 along the central axis of the valve stent 200. The peripheral surfaces of the plurality of lugs 230 are preferably cylindrical.

Figure 18:
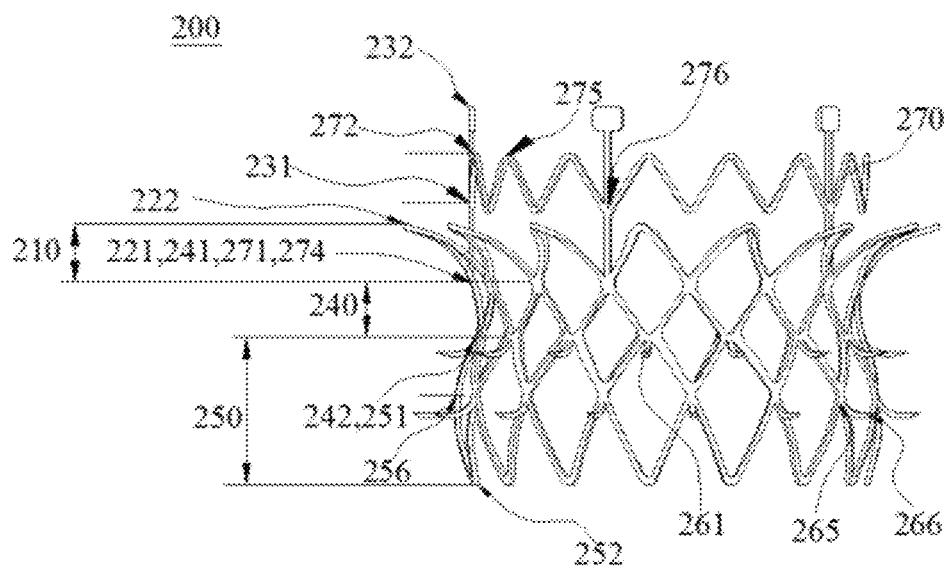
FIG. 18 is a schematic structural diagram of yet another valve stent in an expanded state according to Embodiment 2 of the present application.

FIG. 18 is a schematic structural diagram of yet another valve stent in an expanded state according to Embodiment 2 of the present application. Referring to FIG. 18, the extension structure 270 includes a group of fourth wave rod units. The fourth wave rod unit includes a plurality of Y-shaped fourth wave rods and a plurality of V-shaped fourth wave rods. Each of the Y-shaped fourth wave rods has a first connection end 274 and two second connection ends 275, and each of the V-shaped fourth wave rods has a second connection end 275. The plurality of Y-shaped fourth wave rods and the plurality of V-shaped fourth wave rods are connected by means of the second connection end 275. The first connection end 274 is fixedly connected to the first end portion 221 of the ring structure 220. The third end portion 231 of the lug 230 is fixedly connected to the fourth node 276. As shown in FIG. 18, the number of the Y-shaped fourth wave rods in FIG. 18 is less than that of the Y-shaped fourth wave rods in FIG. 13. The connection between the extension structure 270 and the ring structure in FIG. 18 is more flexible.

In this embodiment, taking the release of the valve stent 200 into the heart through the left atrial approach as an example, the process of releasing the valve stent 200 into the natural mitral valve by a delivery system is explained.

First, the valve stent 200 is compressed into the sheath of the delivery system from the proximal end of the sheath. In this case, the valve stent 200 is separated from the natural mitral valve.

Secondly, the valve stent 200 is pushed to the distal end of the sheath by means of a pusher of the delivery system, and the valve stent 200 is released at the distal end of the sheath.

During the release of the valve stent 200 at the distal end of the sheath, the outflow tract structure 250 and the transition tract structure 240 of the valve stent 200 are sequentially released from the sheath. The part of the valve stent 200 released from the sheath is automatically expanded and appears to be a conical structure when compared with the sheath.

The valve stent 200 is continuously released, and the barbs begin to pierce into the leaflets and annulus of the natural mitral valve. In this case, the valve stent 200 can still be retrieved as a whole into the sheath.

The valve stent 200 is continuously released, and the ring structure 220 of the inflow tract structure 210 is released from the sheath. In this case, a part of the extension structure 270 is still located in the sheath, and the lug 230 is still not released from the sheath.

The valve stent 200 is continuously released, until the extension structure 270 and the lug 230 are completely released from the sheath.

Figure 19:
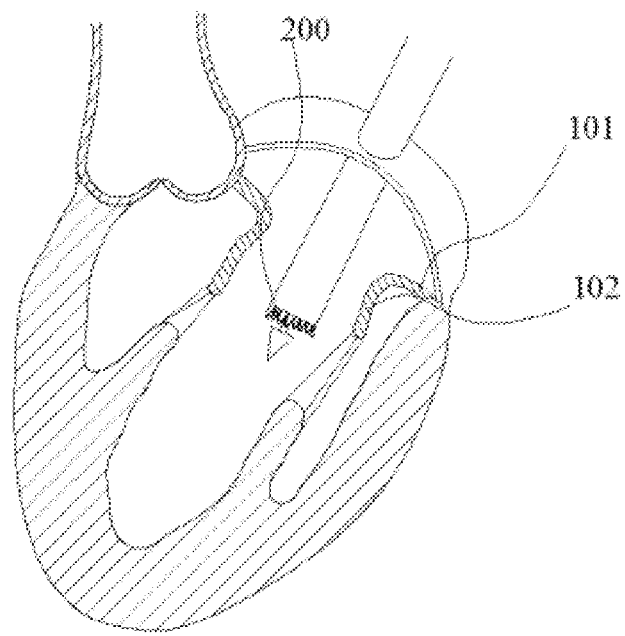
FIG. 19 is a schematic diagram showing release of a part of the valve stent from a sheath according to Embodiment 2 of the present application.
Figure 20:
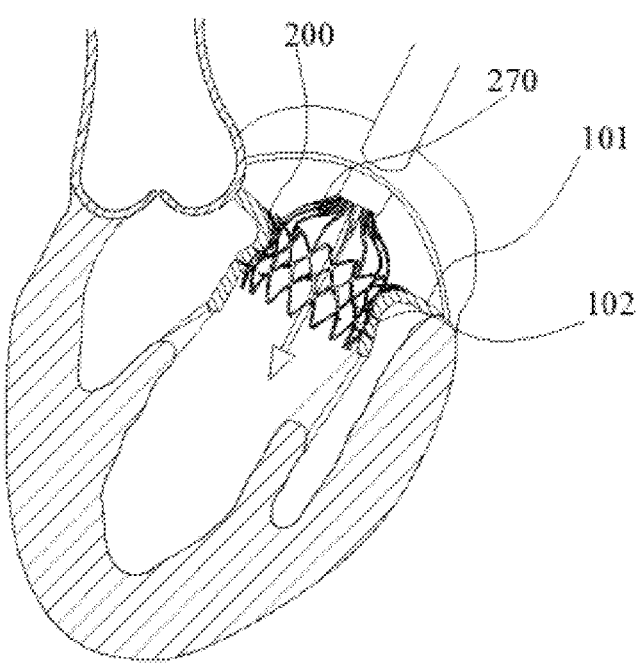
FIG. 20 is another schematic diagram showing release of a part of the valve stent from a sheath according to Embodiment 2 of the present application.
Figure 21:
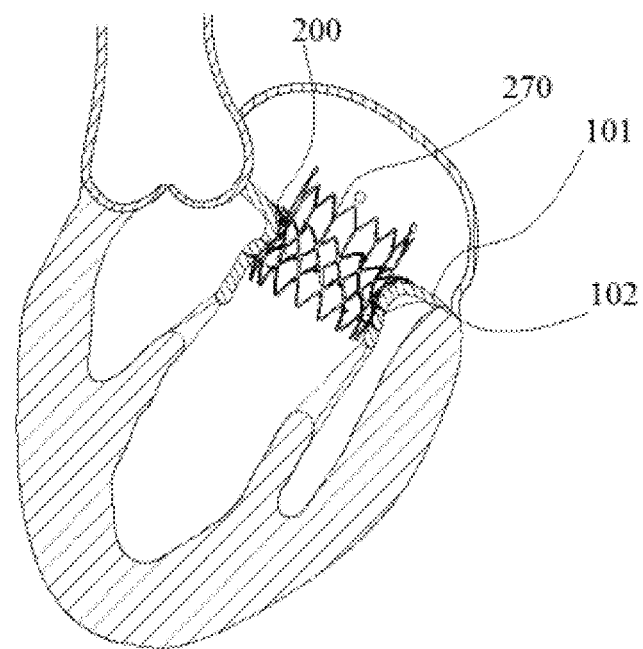
FIG. 21 is a schematic diagram showing that a part of the valve stent is completely released from a sheath and anchored in a natural mitral valve according to Embodiment 2 of the present application.

Specifically, reference may be made to FIGS. 19, 20, and 21. FIG. 19 is a schematic diagram showing release of a part of the valve stent from a sheath according to Embodiment 2 of the present application. FIG. 20 is another schematic diagram showing release of a part of the valve stent from a sheath according to Embodiment 2 of the present application. FIG. 21 is a schematic diagram showing that a part of the valve stent is completely released from a sheath and anchored in a natural mitral valve according to Embodiment 2 of the present application.

As shown in FIG. 19, the outflow tract structure 250 comes out of the sheath first when the valve stent 200 begins to be released from the sheath. As shown in FIG. 20, when the valve stent 200 is released into the natural mitral valve, the valve stent 200 expands. In this case, the barb structure is anchored onto the leaflets and annulus of the natural mitral valve. Under the compression of the valve stent 200, the annulus and leaflets of the natural mitral valve fill in the inward recess of the transition tract structure 240, and cover the peripheral surface of the transition tract structure 240. Part of the extension structure 270 and all the lugs 230 are still located in the sheath. As shown in FIG. 21, when the valve stent 200 is completely released into the natural mitral valve and anchored on the natural mitral valve, the barb structure is anchored on the leaflets and annulus of the natural mitral valve, and the ring structure 220 covers the annulus of the natural mitral valve, that is, covers the ostium of the inflow tract structure of the left ventricle, and the extension structure 270 and the lug 230 are located in the left atrium.

Embodiment 3

Figure 22:
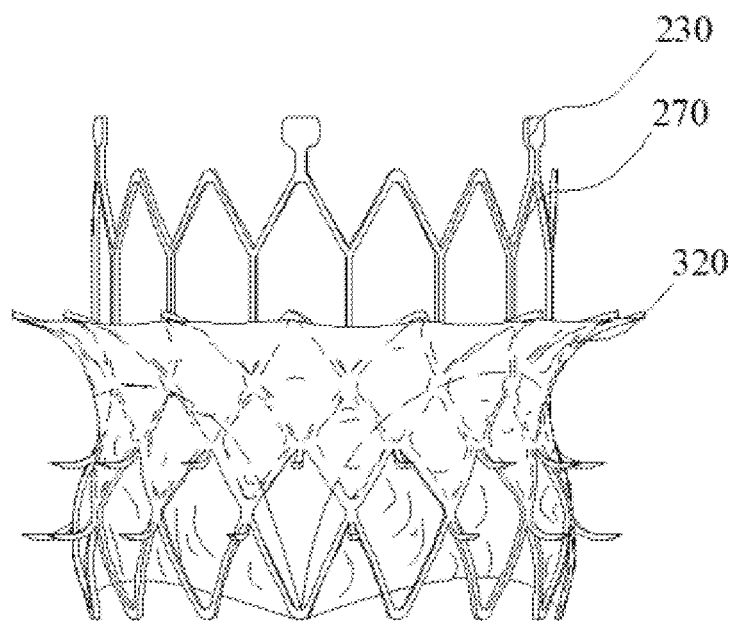
FIG. 22 is a front view of a valve prosthesis in an expanded state according to Embodiment 3 of the present application.
Figure 23:
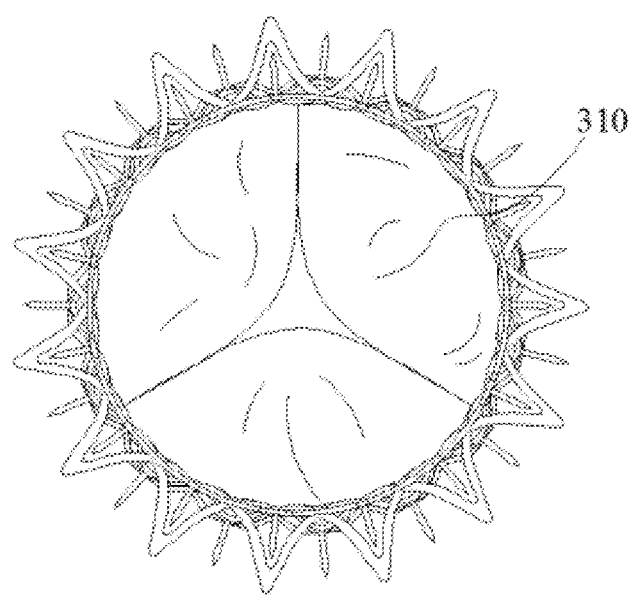
FIG. 23 is a top view of a valve prosthesis in an expanded state according to Embodiment 3 of the present application.

This embodiment provides a valve prosthesis. Referring to FIGS. 22 and 23, FIG. 22 is a front view of a valve prosthesis in an expanded state according to Embodiment 3 of the present application, and FIG. 23 is a top view of a valve prosthesis in an expanded state according to Embodiment 3 of the present application. For example, the valve prosthesis includes the valve stent 200 in the foregoing embodiments and a valve assembly.

The valve assembly is attached to the valve stent 200. The valve assembly includes a prosthetic leaflet 310 (referring to FIG. 23) and a suture skirt 320 (referring to FIG. 22).

In this embodiment, the prosthetic leaflet 310 and the suture skirt 320 are attached to the valve stent 200 by means of suture.

The prosthetic leaflet 310 is sutured inside the transition tract structure 240 and the outflow tract structure 250, and the prosthetic leaflet 310 is used to make blood to flow through the inside of the valve stent 200 from the inflow tract structure 210 to the outflow tract structure 250, so as to replace the natural mitral valve to realize a one-way valve function, thereby preventing blood from entering the left atrium from the left ventricle. In this embodiment, as shown in FIG. 23, there are three leaflets. In other embodiments, the number of the leaflets may be two or more.

The suture skirt 320 covers the ring structure 220, the transition tract structure 240, and the outflow tract structure 250. The suture skirt 320 does not cover the extension structure 270 and the lug 230. The suture skirt 320 preferably covers the peripheral surfaces of the ring structure 220, the transition tract structure 240 and the outflow tract structure 250. The suture skirt 320 is used to prevent blood flowing from the left atrium into the left ventricle through the peripheral surfaces of the ring structure 220, the transition tract structure 240 and the outflow tract structure 250. That is, the suture skirt 320 can only allow blood to flow from the left atrium into the left ventricle through the prosthetic leaflet 310, and thus, the blood circulation path is single, so as to avoid forming thrombosis between the valve prosthesis and the annulus and leaflets of the natural mitral valve.

The prosthetic leaflets 310 and the suture skirt 320 can be animal pericardium after biological treatment or other biocompatible polymer materials.

After the valve prosthesis is implanted in the heart, the ring structure 220 covers the annulus of the natural mitral valve, the transition tract structure 240 and the outflow tract structure 250 are located on the annulus and leaflets of the natural mitral valve, the barb structure pierces into the annulus and leaflets of the natural mitral valve, and the annulus and leaflets of the natural mitral valve are filled into the recess formed by the transition tract structure 240 and the barb structure under the compression of the valve prosthesis, so that the annulus and leaflets of the natural mitral valve cover the peripheral surfaces of the transition tract structure 240 and the outflow tract structure 250. When the heart is dilated, the prosthetic leaflet 310 opens naturally due to the impact of blood, allowing blood to enter the left ventricle from the left atrium. Due to the function of the suture skirt 320, blood is prevented from entering the left ventricle from the left atrium through the gap between the annulus and leaflets of the natural mitral valve and the peripheral surface of the valve prosthesis. The pressure in the left ventricle rises and the prosthetic leaflets 310 close when the heart contracts. Under the action of the suture skirt 320 and the influence of filling the natural mitral valve into the recess of the transition tract structure 240, blood cannot flows through the valve prosthesis into the left atrium when the heart contracts. Therefore, the valve prosthesis replaces the natural mitral valve to realize the function of a one-way valve.

In this embodiment, taking the release of the valve prosthesis having the valve stent in Embodiment 2 into the heart through the left atrial as an example, the process of releasing the valve prosthesis into the natural mitral valve by a delivery system is explained.

First, the valve prosthesis is compressed into the sheath of the delivery system from the proximal end of the sheath. In this case, the valve prosthesis is separated from the natural mitral valve.

Secondly, the valve prosthesis is pushed to the distal end of the sheath by means of a pusher of the delivery system, and the valve prosthesis is released at the distal end of the sheath.

During the release of the valve prosthesis at the distal end of the sheath, an outflow tract structure and a transition tract structure of the valve prosthesis are sequentially released from the sheath. The part of the valve prosthesis released from the sheath is automatically expanded and appears to be a conical structure when compared with the sheath.

The valve prosthesis is continuously released, and the barbs begin to pierce into the leaflets and annulus of the natural mitral valve. In this case, the valve prosthesis can still be retrieved as a whole into the sheath.

The valve prosthesis is continuously released, and a ring structure of the inflow tract structure is released from the sheath. In this case, a part of an extension structure is still located in the sheath, and a lug is still not released from the sheath.

The valve prosthesis is continuously released, until the extension structure and the lug are completely released from the sheath.

The above description is only a description of the preferred embodiments of the present application, and is not intended to limit the scope of the present application. Any changes and modifications made by those skilled in the art according to the above disclosure are all within the scope of protection of the claims.

What is claimed is:

1. A valve stent, wherein the valve stent is a self-expanding stent, is shaped as a mesh tube, and has a compressed state and an expanded state;
the valve stent comprises an inflow tract structure, a transition tract structure, an outflow tract structure, and at least one first barb; the inflow tract structure, the transition tract structure, and the outflow tract structure are connected sequentially, and the at least one first barb is disposed on the outflow tract structure;
the inflow tract structure comprises a ring structure having a first end portion and a second end portion, and the second end portion is a free end; in the expanded state, a diameter of a radial section of the first end portion of the ring structure is smaller than a diameter of a radial section of the second end portion of the ring structure;
the transition tract structure has a fifth end portion, a sixth end portion, and a first middle section; the fifth end portion and the sixth end portion are located at two ends of the first middle section in an axial direction of the first middle section; the fifth end portion is fixedly connected to the first end portion of the ring structure; the sixth end portion is away from the inflow tract structure; in the expanded state, diameters of radial sections of the fifth end portion and the sixth end portion are greater than a diameter of a radial section of the first middle section of the transition tract structure;
the outflow tract structure has a seventh end portion, an eighth end portion, and a second middle section; the seventh end portion and the eighth end portion are located at two ends of the second middle section in an axial direction of the second middle section; the seventh end portion of the outflow tract structure is fixedly connected to the sixth end portion of the transition tract structure; the eighth end portion is away from the transition tract structure and the inflow tract structure, and the eighth end portion is a free end;
the at least one first barb protrudes towards an outside of the outflow tract structure, and extends towards the free end of the outflow tract structure.

2. The valve stent according to claim 1, further comprising a plurality of second barbs; wherein the at least one first barb comprises a plurality of said first barbs; each of the first barbs and the second barbs has a fixation end; one end of each of the first barbs and the second barbs away from the fixation end is a free end; the fixation end of each of the second barbs is disposed on the transition tract structure, and each of the second barbs protrude from the fixation end thereof towards the outside of the transition tract structure; the fixation end of each of the first barbs is located on the outflow tract structure, and each of the first barbs protrude from the fixation end thereof towards the outside of the outflow tract structure.

3. The valve stent according to claim 2, wherein the fixation end of each of the second barbs is located on the sixth end portion of the transition tract structure, and the fixation end of each of the first barbs is located on the outflow tract structure.

4. The valve stent according to claim 3, wherein in the expanded state, a diameter of a radial section of the seventh end portion and a diameter of a radial section of the eighth end portion are smaller than a diameter of a radial section of the second middle section, a section with a maximum diameter among radial sections of the outflow tract structure is a first section, and each of the first barbs is located in the first section of the outflow tract structure.

5. The valve stent according to claim 1, comprising an extension structure having a ninth end portion and a tenth end portion, wherein the ninth end portion is fixedly connected to the ring structure, and the tenth end portion is away from the ring structure and the transition tract structure.

6. The valve stent according to claim 5, wherein an axial length of the extension structure is greater than an axial length of the ring structure after the valve stent is compressed.

7. The valve stent according to claim 5, wherein an axial length of the extension structure is smaller than an axial length of the ring structure after the valve stent is compressed.

8. The valve stent according to claim 5, wherein the inflow tract structure and the extension structure are staggered apart from each other in an axial direction after the valve stent is compressed.

9. The valve stent according to claim 5, wherein a maximum diameter of radial sections of the extension structure is smaller than a maximum diameter of radial sections of the ring structure.

10. The valve stent according to claim 5, wherein the ninth end portion of the extension structure is fixedly connected to the first end portion of the ring structure.

11. The valve stent according to claim 5, further comprising a plurality of lugs, wherein the tenth end portion of the extension structure is fixedly connected to the lugs.

12. The valve stent according to claim 5, wherein the extension structure comprises at least a group of fourth wave rod units, and the group of fourth wave rod units comprises a plurality of Y-shaped fourth wave rods.

13. The valve stent according to claim 1, comprising an extension structure having a ninth end portion and a tenth end portion, wherein the ninth end portion is fixedly connected to the transition tract structure, and the tenth end portion is away from the transition tract structure.

14. The valve stent according to claim 1, wherein in the expanded state, a sum of axial lengths of the outflow tract structure and the transition tract structure is in a range of 10 mm to 35 mm.

15. The valve stent according to claim 1, wherein a radial section of the ring structure of the valve stent has a shape of a circular ring, an elliptical ring, or a D-shaped ring.

16. A valve prosthesis, comprising a valve stent, a prosthetic leaflet, and a suture skirt, wherein the valve stent is a self-expanding stent, is shaped as a mesh tube, and has a compressed state and an expanded state;

the valve stent comprises an inflow tract structure, a transition tract structure, an outflow tract structure, and at least one first barb; the inflow tract structure, the transition tract structure, and the outflow tract structure are connected sequentially, and the at least one first barb is disposed on the outflow tract structure;

the inflow tract structure comprises a ring structure having a first end portion and a second end portion, and the second end portion is a free end; in the expanded state, a diameter of a radial section of the first end portion of the ring structure is smaller than a diameter of a radial section of the second end portion of the ring structure;

the transition tract structure has a fifth end portion, a sixth end portion, and a first middle section; the fifth end portion and the sixth end portion are located at two ends of the first middle section in an axial direction of the first middle section; the fifth end portion is fixedly connected to the first end portion of the ring structure; the sixth end portion is away from the inflow tract structure; in the expanded state, diameters of radial sections of the fifth end portion and the sixth end portion are greater than a diameter of a radial section of the first middle section of the transition tract structure;

the outflow tract structure has a seventh end portion, an eighth end portion, and a second middle section; the seventh end portion and the eighth end portion are located at two ends of the second middle section in an axial direction of the second middle section; the seventh end portion of the outflow tract structure is fixedly connected to the sixth end portion of the transition tract structure; the eighth end portion is away from the transition tract structure and the inflow tract structure, and the eighth end portion is a free end;

the at least one first barb protrudes towards an outside of the outflow tract structure, and extends towards the free end of the outflow tract structure;

wherein the prosthetic leaflet and the suture skirt are attached to the valve stent; the prosthetic leaflet is located inside the transition tract structure and the outflow tract structure; the suture skirt covers the ring structure, the transition tract structure, and the outflow tract structure; wherein a single blood channel, configured to allow blood to flow through an interior of the valve stent in a direction from the inflow tract structure to the outflow tract structure, is formed by the suture skirt and the prosthetic leaflet.

17. The valve prosthesis of claim 16, wherein the valve stent further comprises an extension structure having a ninth end portion and a tenth end portion, wherein the ninth end portion is fixedly connected to the ring structure, and the tenth end portion is away from the ring structure and the transition tract structure; wherein the suture skirt is not attached to the extension structure.

* * * * *